(12) United States Patent
van't Hof et al.

(10) Patent No.: US 11,273,076 B2
(45) Date of Patent: Mar. 15, 2022

(54) ACOUSTIC VALVE AND EAR PLUG FOR HEARING PROTECTION

(71) Applicant: Dynamic Ear Company B.V., Delft (NL)

(72) Inventors: Pieter Gerard van't Hof, Delft (NL); Engbert Wilmink, Delft (NL)

(73) Assignee: SONOVA AG, Staefa (CH)

( * ) Notice: Subject to any disclaimer, the term of this patent is extended or adjusted under 35 U.S.C. 154(b) by 410 days.

(21) Appl. No.: 15/326,249

(22) PCT Filed: Jul. 16, 2015

(86) PCT No.: PCT/NL2015/050522
§ 371 (c)(1),
(2) Date: Jan. 13, 2017

(87) PCT Pub. No.: WO2016/010431
PCT Pub. Date: Jan. 21, 2016

(65) Prior Publication Data
US 2017/0202710 A1    Jul. 20, 2017

(30) Foreign Application Priority Data

Jul. 17, 2014   (NL) .................................... 2013208

(51) Int. Cl.
*A61F 11/08*    (2006.01)
(52) U.S. Cl.
CPC ......... *A61F 11/08* (2013.01); *A61F 2011/085* (2013.01)
(58) Field of Classification Search
CPC .......... A61F 11/06; A61F 11/08; A61F 11/10; A61F 11/12; A61F 2011/085;
(Continued)

(56) References Cited

U.S. PATENT DOCUMENTS 4,441,576 A * 4/1984 Allen ...................... A61F 11/08
                                                   128/867
4,540,063 A * 9/1985 Ochi ...................... A61F 11/08
                                                   128/867
(Continued)

FOREIGN PATENT DOCUMENTS

CN         1897896 A      1/2007
CN       101626745 A      1/2010
(Continued)

OTHER PUBLICATIONS

International Search Report dated Oct. 1, 2015 for Appln. No. PCT/NL2015/050522.

(Continued)

*Primary Examiner* — Alireza Nia
*Assistant Examiner* — Kevin S Albers
(74) *Attorney, Agent, or Firm* — Pillsbury Winthrop Shaw Pittman, LLP

(57) ABSTRACT

The present disclosure concerns an acoustic valve (10) for hearing protection. The valve (10) comprises a housing (1) that is placeable or integrated in an ear plug (100). The housing (1) comprises a sound passage (2) extending through the housing (1) for allowing at least partial transmission of sound from the external surroundings (11) into the auditory canal (13). The housing comprises an impulse filter (3) comprising a rigid plate (4). The rigid plate (4) forms an enclosed volume (12) within the sound passage (2) of the valve. The rigid plate (4) comprises at least one perforation (5) for passing part of the sound from the external surroundings (11) via the perforation (5) into the enclosed volume (12). The housing further comprises an acoustic filter (6) comprising a mesh (7) arranged in the sound passage (2) between the rigid plate (4) and the auditory canal (13).

20 Claims, 9 Drawing Sheets

(58) Field of Classification Search
CPC ............ A61F 2011/145; A61F 13/2017; A61F 2002/183; A61F 2011/08; A61F 11/14; H04R 1/1016; H04R 25/00; H04R 25/02; Y10S 514/956; A61B 5/00; A61B 5/6816; A61B 5/6817; F16K 47/04; A42B 3/16; A42B 3/166; A42B 3/163
USPC ............... 128/857, 864, 865, 866, 867, 868; 181/130, 132, 135; 381/380, 328, 72, 381/322
See application file for complete search history.

(56) References Cited

U.S. PATENT DOCUMENTS

| | | | | |
|---|---|---|---|---|
| 5,864,628 | A * | 1/1999 | Posen | H04R 25/654 |
| | | | | 381/325 |
| 6,068,079 | A * | 5/2000 | Hamery | A61F 11/08 |
| | | | | 128/864 |
| 6,148,821 | A * | 11/2000 | Falco | A61F 11/08 |
| | | | | 128/864 |
| 6,286,622 | B1 * | 9/2001 | Tiemann | A61F 11/08 |
| | | | | 128/864 |
| 8,054,985 | B2 * | 11/2011 | Doty | A61F 11/08 |
| | | | | 381/72 |
| 2007/0009132 | A1 * | 1/2007 | Miller, III | H04R 25/606 |
| | | | | 381/369 |
| 2007/0183606 | A1 | 8/2007 | Doty | |
| 2010/0329475 | A1 * | 12/2010 | Killion | A61F 11/08 |
| | | | | 381/72 |
| 2012/0077010 | A1 * | 3/2012 | Manesis | B29C 67/20 |
| | | | | 428/220 |

FOREIGN PATENT DOCUMENTS

| | | | | |
|---|---|---|---|---|
| EP | 1 527 761 | | 5/2005 | |
| GB | 2458 538 | | 9/2009 | |
| GB | 2458538 A | * | 9/2009 | ............. A61F 11/08 |
| WO | 2011/078659 A1 | | 6/2011 | |
| WO | WO 2011/078659 | | 6/2011 | |

OTHER PUBLICATIONS

First Office Action issued in corresponding Chinese Patent Application No. 201580038187.7 dated Sep. 5, 2018 with English translation.

* cited by examiner

ACOUSTIC VALVE AND EAR PLUG FOR HEARING PROTECTION

CROSS-REFERENCE TO RELATED APPLICATIONS

This is the U.S. National Stage of PCT/NL2015/050522, filed Jul. 16, 2015, which in turn claims priority to Netherlands Application No. 2013208, filed Jul. 17, 2014, the entire contents of both applications being incorporated herein by reference in their entireties.

TECHNICAL FIELD AND BACKGROUND

The present disclosure relates to an acoustic valve for hearing protection. The disclosure further relates to an ear plug for hearing protection comprising the acoustic valve.

It is recognized that people can be exposed in their daily life to unwanted sounds and sound levels. Excessive sound levels may even cause temporary or permanent damage to a person's hearing. To protect against unwanted or excessive sound, various devices exist that form a barrier or filter between the ear canal and the external surroundings. For example, an ear plug for hearing protection may comprise a universal or customized tip with an outer contour for sealingly fitting into an auditory canal of a user. The earplug may provide a general blocking of all environmental sound. However, this may also prevent the user from hearing any other sound, e.g. speech, which can be undesired in some circumstance. For example, military or law enforcement officers may desire to have a good sense of hearing for regular environmental sound while at the same time being protected against excessive sound levels, e.g. from gunshots. Accordingly, a non-linear filtering of different sound levels can be desired, wherein excessive sound levels are more attenuated than lower sound levels.

U.S. Pat. No. 6,068,079 describes an acoustic valve capable of selective and non-linear filtering of sound and placeable in a perforated ear plug. The acoustic valve consists of a tube enclosing two rigid disks axially spaced opposite each other, each of the disks containing at least one perforation. The total perforated surface of at least one disk is between 0.03 and 0.5 mm2 (square millimetre). It is appreciated that the prior art device may provide a simple design to protect against excessive (impulse) sound levels while at the same time allowing at least a perception of regular sound levels. However, it is found that the overall hearing perception of the environment can feel artificial to a user of the device.

Accordingly there is a desire for a simple design hearing protection device that provides a more natural hearing perception of the environment.

SUMMARY

According to one aspect, the present disclosure provides an acoustic valve for hearing protection, the valve comprising a housing placeable or integrated in an ear plug to form a seal between an auditory canal of an ear and an external surroundings, the housing comprising a sound passage extending through the housing for allowing at least partial transmission of sound from the external surroundings into the auditory canal; an impulse filter comprising a rigid plate forming an enclosed volume within the sound passage, wherein the rigid plate comprises at least one perforation for passing part of the sound from the external surroundings via the perforation into the enclosed volume; and an acoustic filter comprising a mesh arranged in the sound passage between the rigid plate and the auditory canal. According to another or further aspect, the present disclosure provides an ear plug for hearing protection comprising a tip with an outer contour for sealingly fitting into an auditory canal of a user, wherein the tip comprises a channel trough the tip, and wherein an acoustic as described herein is arranged in the channel.

Without wishing to be bound by theory, it is appreciated that the synergetic combination of a rigid perforated plate or disc, a mesh, and an enclosed volume, can provide a more natural hearing perception in a simple hearing protection device. The mesh, which is typically woven, can provide a attenuation in particular at relatively low sound levels while the impulse filter, formed by the rigid perforated plate and the enclosed volume therein between, can provide attenuation in particular at relatively high sound levels. The combined arrangement can provide a relatively flat acoustic transfer function, which is found to be associated with a more natural perception of environmental sound.

The inventors find that a single perforated rigid disc can be used to form an enclosed volume in combination with the acoustic filter and thereby used as an impulse filter. By forming the enclosed volume between the rigid plate and the acoustic filter, in particular the mesh, a more compact arrangement can be provided than e.g. by a combination of an acoustic filter with two perforated discs. The compact arrangement can be of particular benefit in an ear plug where spacing is limited.

To provide a barrier for impulse sound while at the same time allowing transfer of naturally occurring sound levels, it is found advantageous to provide a total perforated cross-section in the rigid plate between 0.01 and 0.10 square millimetre, preferably between 0.025 and 0.035 square millimetre. Alternatively, or in addition, the impulse filter is found to provide improved performance, i.e. sufficient protection while allowing natural audio perception, when a specific size is provided for the enclosed volume. Accordingly, the enclosed volume, e.g. between the rigid plate and the mesh, is preferably selected in a range between 5 and 20 cubic millimetre, more preferably between 10 and 15 cubic millimetre. Also a thickness of the rigid plate at a position of the perforation is found to influence the sound transfer function. To provide improved performance, this thickness is preferably chosen in a range between 0.05 and 0.5 millimetre, more preferably between 0.1 and 0.3 millimetre.

By providing the rigid plate as an integral part of the housing, production of the device can be simplified. For example, the housing and/or perforated rigid plate can be made from plastic, e.g. by a moulding technique. The rigid disc or plate may also comprise a metal part, e.g. produced by an etch technique. The metal part may provide improved rigidity to the plate which can be beneficial for blocking excessive sound. In any case, the impulse filter is preferably arranged for attenuating impulse sound, e.g. above 130 dB, from the external surroundings into the auditory canal.

The mesh is preferably a woven mesh, e.g. precision woven. It is found that the sound filtering characteristics of a mesh can be particularly beneficial for attenuating relatively low to midrange sound pressure levels, e.g. below 100 dB. The characteristics of the mesh can be determined e.g. by the many openings formed between a woven grid of the mesh. Typically, several hundred openings can be formed which however provide a relatively low total cross-section. To provide adequate attenuation, the cross-section surface of the openings is preferably between 1 to 20 percent of the total cross-section surface of the mesh, more preferably between 12 and 15 percent.

As described above, the combination of the rigid disc and mesh can provide a simple yet effective means for improving natural perception, in particular for a combination of relatively low and relatively high sound levels. The perception may be even further enhanced by the provision of further acoustic filtering elements. In this regard it is found that a flexible membrane can be provided between the perforated disc and the mesh to enhance filtering of sounds traversing the perforation of the rigid plate. For example, the flexible membrane may flex towards the mesh at elevated sound pressure levels in the enclosed volume. By placing the flexible membrane relatively close to the mesh, e.g. closer than 0.15 millimetre in equilibrium (without sound), the flexible membrane may abutting against the mesh at elevated sound pressure levels, e.g. at sound pressure levels in the enclosed volume above 120 dB. Overall, the flexible membrane may thus provide a further flattening effect on the acoustic transfer function and improve natural perception.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
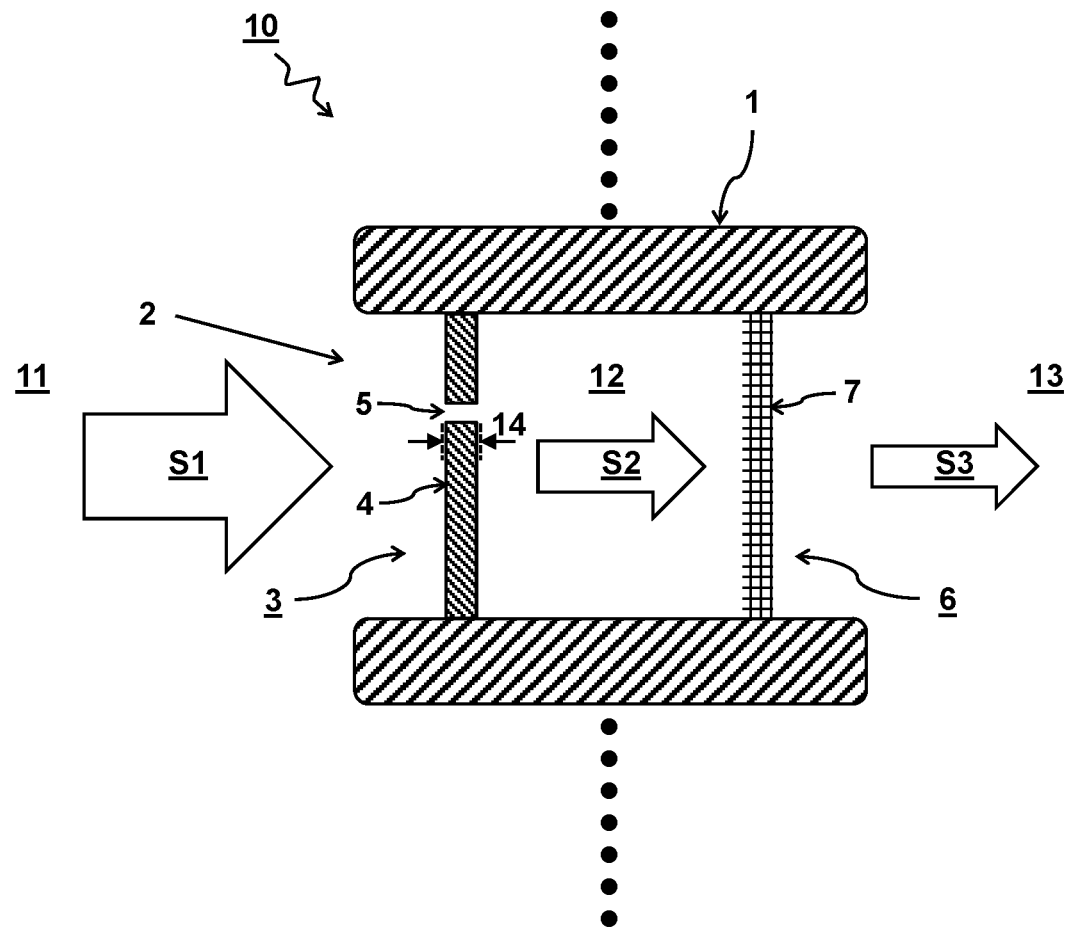
FIG. 1 shows a schematic cross section view of an embodiment of an acoustic valve.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1 shows a schematic cross section view of an embodiment of an acoustic valve 10 that can be used for hearing protection.

In one embodiment, as shown, the valve 10 comprises a housing 1. The housing can be placeable or integrated in an ear plug 100. The combined ear plug with acoustic valve may form a seal or filter between an auditory canal 13 of an ear and an external surroundings 11. The housing 1 comprises a sound passage 2 extending through the housing 1. The sound passage 2 is arranged for allowing at least partial, e.g. filtered or, damped, transmission of sound from the external surroundings 11 into the auditory canal 13 via the acoustic elements placed therein.

In one embodiment, the sound passage 2 comprises an impulse filter 3. The impulse filter 3 comprises a rigid plate 4 forming an enclosed volume 12 within the sound passage 2. The rigid plate 4 comprises at least one perforation 5 for passing part of the sound from the external surroundings 11 via the perforation 5 into the enclosed volume 12. The rigidity of the plate 4 is preferably such as to provide minimal or no transmission of sound waves via the plate structure 4 itself, and substantially exclusively via the perforation 5.

In one embodiment, the sound passage 2 comprises an acoustic filter 6. The acoustic filter 6 comprises a mesh 7. In the embodiment shown, the mesh 7 is arranged in the sound passage 2 between the rigid plate 4 and the auditory canal 13. This arrangement provides an advantageous sequence of filtering the relatively loud noises before passing the sound to the mesh. Overall, the combination of the rigid plate 4 and mesh 7 can provide a relatively flat and/or smooth acoustic transfer function compared e.g. to a combination of perforated rigid plates.

In use, sound S1 from the external surroundings 11 enters the sound passage 2 of the valve 10. The sound S2 that passes the rigid plate 4 via perforation 5, enters into the enclosed volume 12. The sound S3 that passes the acoustic filter 6, in this case mesh 7, enters into the auditory canal 13 of a user.

In one embodiment, a cross-section of the perforation 5 in the rigid plate 4 is between 0.01 and 0.10 square millimetre. In one embodiment, a plurality of perforations is provided having a total perforated cross-section within the said range. For example, two, three, or more perforations can be provided in the rigid plate 4. However, an increased number of perforations can affect the acoustic transfer function. Accordingly, it is found desirable to keep the number of perforations in the rigid disc at fifty or below, preferably at twenty or below, more preferably at ten or below, most preferable at five or below. The less the number of perforations in the rigid disc, the higher can be the individual cross section of the perforations. A higher cross-section of a perforation, may be associated with a lower capillary resistance, which may affect the acoustic transfer function. Similarly, a lower thickness 14 of the rigid plate 4 may be associated with a lower capillary resistance. For example, in one embodiment, a thickness 14 of the rigid plate 4 at the at least one perforation 5 is between 0.05 and 0.5 millimetre.

In one embodiment, the enclosed or at least substantially enclosed volume 12 is formed between the rigid plate 4 and the acoustic filter 6. In the embodiment shown, the enclosed volume 12 is formed or defined between the rigid plate 4, the mesh 7 and the inner walls of the housing 1. The enclosed volume 12 may act as a buffer to receive sound waves traversing the perforation 5. Together with the rigid plate 4, the enclosed volume 12 may act as an impulse filter 3. In one embodiment, the enclosed volume 12 is between 5 and 20 cubic millimetre. In one embodiment, the impulse filter 3 is arranged for attenuating impulse sound above 130 dB from the external surroundings 11 into the auditory canal 13.

It is noted that the mesh 7 is substantially different from the rigid plate 4 in structure and function. In one embodiment, the mesh 7 comprises a woven structure. For example, a plastic mesh may be extruded, oriented, expanded, woven or tubular. In one embodiment, it comprises a wire mesh. In one embodiment, the mesh 7 comprises a grid forming a plurality of openings through the grid, wherein a cross-section surface of the openings is between 1 to 20 percent of the total cross-section surface of the mesh 7. The structure of the mesh typically provides a relatively low rigidity.

In the embodiment shown, the acoustic filter 6 is formed by the mesh 7. In one embodiment, the acoustic filter 6, e.g. mesh 7, is arranged for flattening an acoustic transfer function of sound from the external surroundings 11 into the auditory canal 13.

Figure 2:
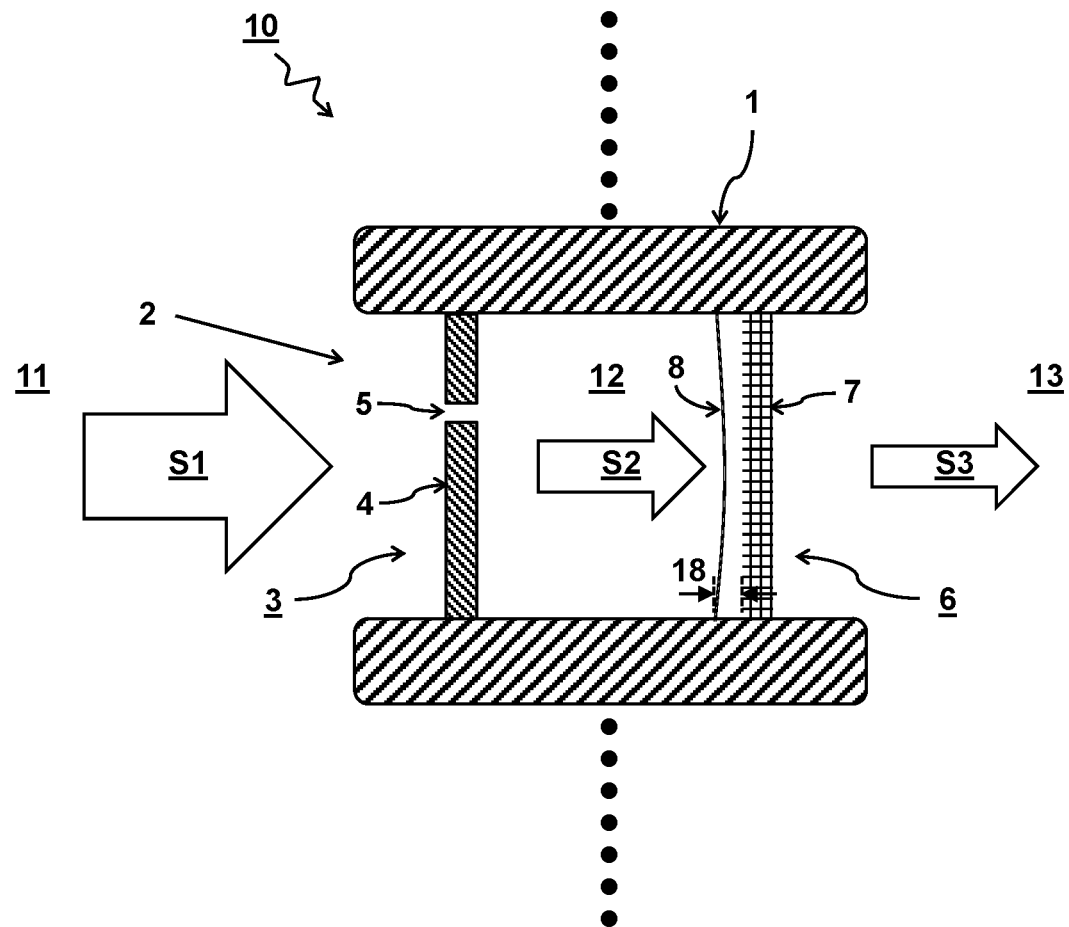
FIG. 2 shows a schematic cross section view of an embodiment of an acoustic valve comprising a flexible membrane.

FIG. 2 shows a schematic cross section view of an embodiment of an acoustic valve 10, similar to FIG. 1, but additionally comprising a flexible membrane 8. In one embodiment, as shown the flexible membrane 8 is arranged between the rigid plate 4 and the mesh 7. In one embodiment, the flexible membrane 8 is arranged for flexing towards the mesh 7 at elevated sound pressure levels in the enclosed volume 12. In one embodiment, the flexible membrane 8 is arranged for abutting the mesh at elevated sound pressure levels in the enclosed volume 12, e.g. above 120 dB. In one embodiment, the flexible membrane 8 is relatively close to the mesh 7. For example, in one embodiment, a distance 18 between the flexible membrane 8 and the mesh 7 (at equilibrium, not flexed) is less than 0.1 millimetre.

The flexible membrane 8 may be considered part of the acoustic filter 6, together with the mesh 7. Together, they may provide a desired acoustic transfer function, in particular for low to mid range sound levels, e.g. up to 120 dB. In combination with the impulse filter 3, an overall relatively flat or smooth transfer function may be obtained. It may be considered that the enclosed volume 12 in one embodiment, is formed between the rigid plate 4 and flexible membrane 8, which may be considered part of the acoustic filter 6. Preferably, the rigid plate 4, flexible membrane 8, and/or mesh 7 are arranged in series and with their respective surfaces transverse to a length of the sound passage 2.

In one embodiment (not shown), the flexible membrane is disposed between a first mesh and a second mesh. In a further embodiment, the flexible membrane is configured for abutting the first mesh at an elevated pressure of the environment relative to the auditory canal, and configured for abutting the second mesh at a lowered pressure of the environment relative to the auditory canal. It will be appreciated that an impulse sound wave may comprise an oscillating pressure level, wherein the flexible membrane configured between two meshes can filter both the over pressure and under pressure regions of the sound wave. In this way, even further improvement to the acoustic transfer function may be obtained.

Figure 3:
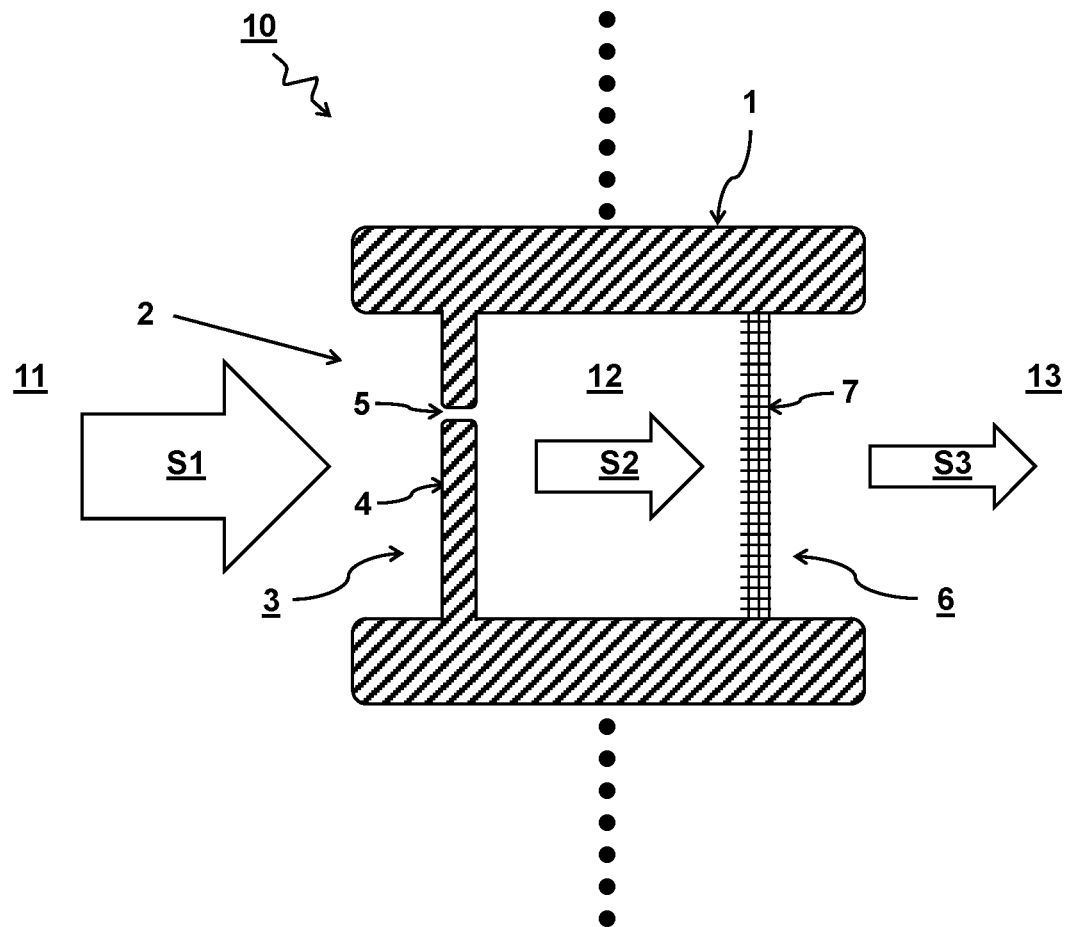
FIG. 3 shows a schematic cross section view of an embodiment of an acoustic valve wherein the rigid perforated plate is part of the housing.

FIG. 3 shows a schematic cross section view of an embodiment of an acoustic valve similar to FIG. 1, except wherein the rigid perforated plate 2 is part of the housing 1, i.e. an integral part of the housing 1. For example, the housing 1 and rigid plate 4 may be produced by a single moulding step, e.g. injection moulding. The perforation 5 may be produced at the time of moulding or applied later.

Figure 4:
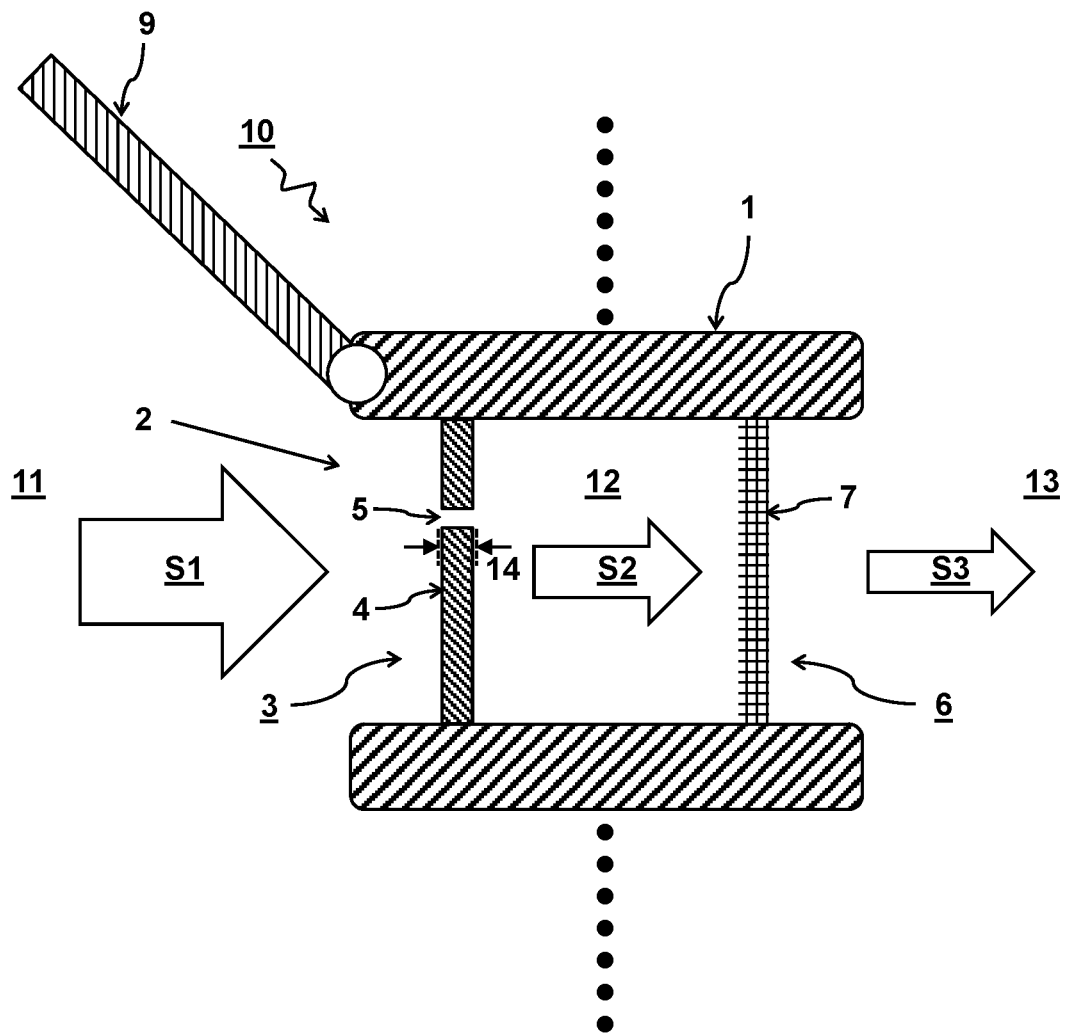
FIG. 4 shows a schematic cross section view of an embodiment of an acoustic valve comprising a switchable cap.

FIG. 4 shows a schematic cross section view of an embodiment of an acoustic valve similar to FIG. 1, but further comprising a switchable cap 9. The cap 9 may be used for fully or partially closing an entrance to the sound passage 2. Accordingly, the cap 9 may act as an additional filter, in case a user wants to further block any sounds from the environment.

Figure 5A:
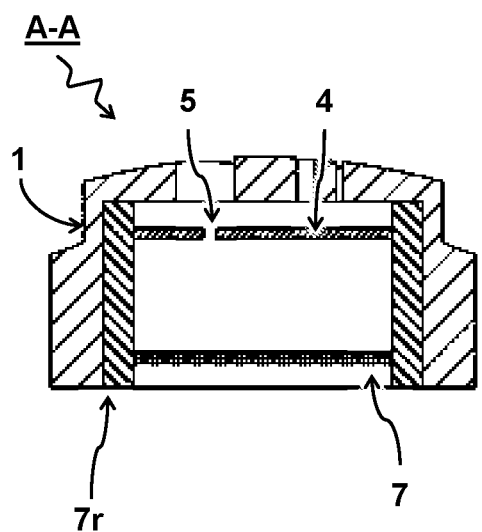
FIGS. 5A-5D show schematic views of an acoustic valve design according to one embodiment.
Figure 5B:
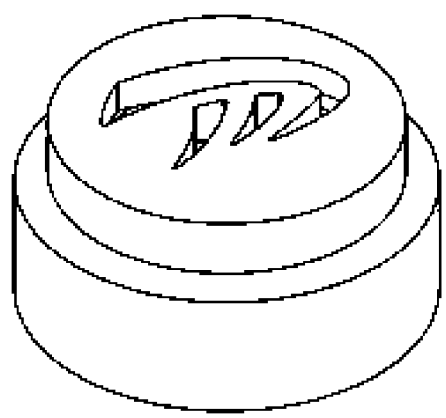
Figure 5C:
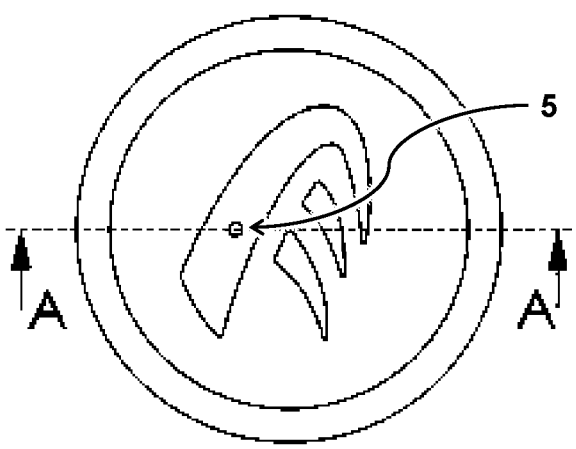
Figure 5D:
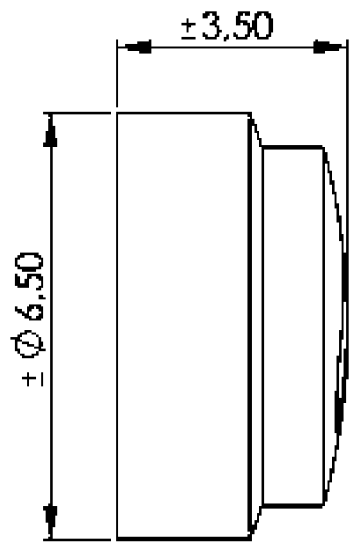

FIGS. 5A-5D show schematic views of a design for an acoustic valve 10 according to one embodiment. FIG. 5A shows a cross section view of section A-A, as viewed along the arrows A, indicated in the top view of FIG. 5C. FIG. 5B shows a perspective view of the embodiment and FIG. 5B shows a side view of the embodiment.

In the embodiment shown, the mesh 7 is spanned by a washer or ring 7r that is placed in the housing 1. Alternatively, the mesh may also be attached directly to the housing. The rigid plate 4 in the embodiment is placed with its perforation 5 in line with an opening in the housing 1, e.g.

a decorative figure or logo cut from the housing 1. The shown measures are given in millimetres, and may vary for different designs. In the embodiment shown, the valve 10, in particular, the housing 1 has an overall round shape. This may advantageously fit to a typical ear plug. However, also other shapes may be used.

Figure 6A:
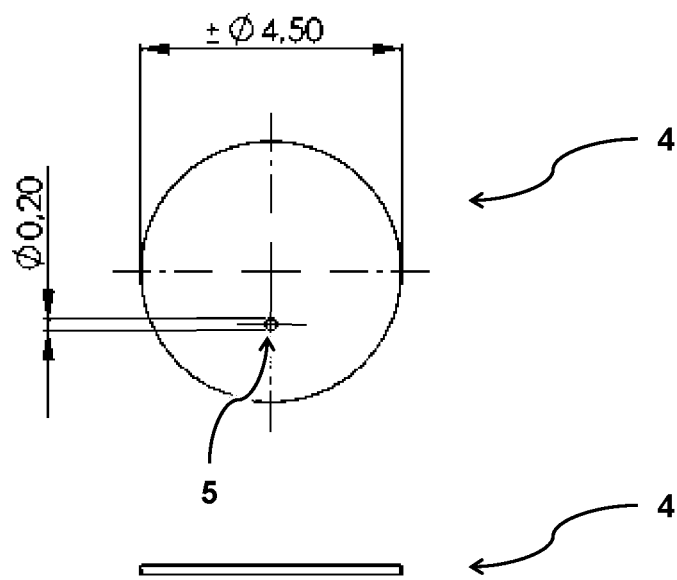
FIG. 6A shows schematic views of a perforated plate design according to one embodiment.

FIG. 6A shows a schematic top and side view of a design according to one embodiment of a rigid plate 4 with perforation 5. Also shown are example measurements for the plate 4, in this case a round disc having a diameter of 4.50 millimetre. The perforation 5, in this example, has a diameter of 0.20 millimetres. The thickness (not indicated here) is for example 0.15 millimetres Also other measure and shapes are possible.

Figure 6B:
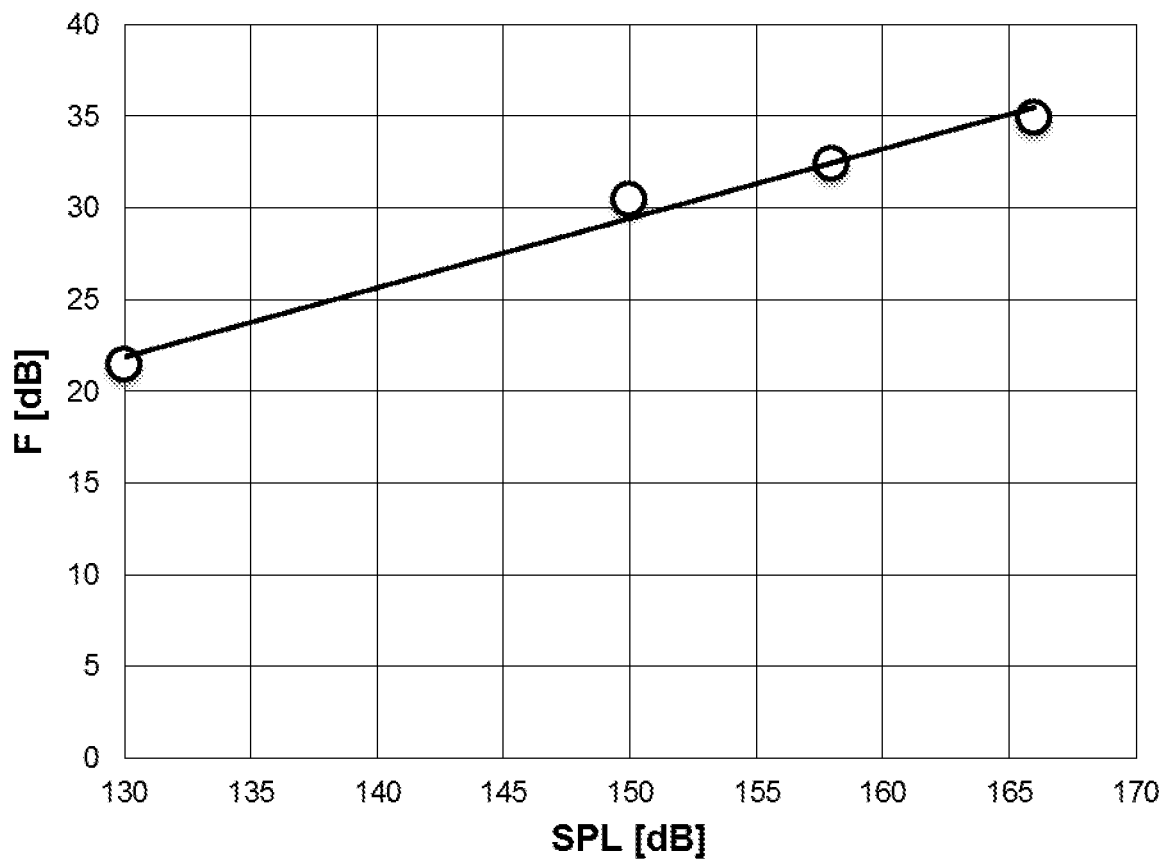
FIG. 6B shows a graph with an example attenuation measurement of an earplug according to one embodiment.

FIG. 6B show an example graph of a measurements for an earplugs having an impulse filter as described herein. In the graph, the attenuation "F" (in decibels, "dB") is plotted as a function of a provided sound pressure level "SPL" at an entrance of the respective ear plug. The SPL indicates an integrated value over a range of frequencies.

In one embodiment, the impulse filter is configured to attenuate impulse sound with an SPL between 140 and 160 dB at the entrance of the earplug to an output SPL below 140 dB at the other end of the earplug. Preferably the sound is attenuated below 130 dB. For example, in the graph, an input SPL of 150 dB is attenuated by 30 dB, to provide an output SPL of 120 dB. An input SPL of 165 dB is attenuated by 35 dB, to provide an output SPL of 130 dB. Accordingly, it is demonstrated that the ear plug can provide an increased attenuation for increased sound pressure levels.

Figure 7A:
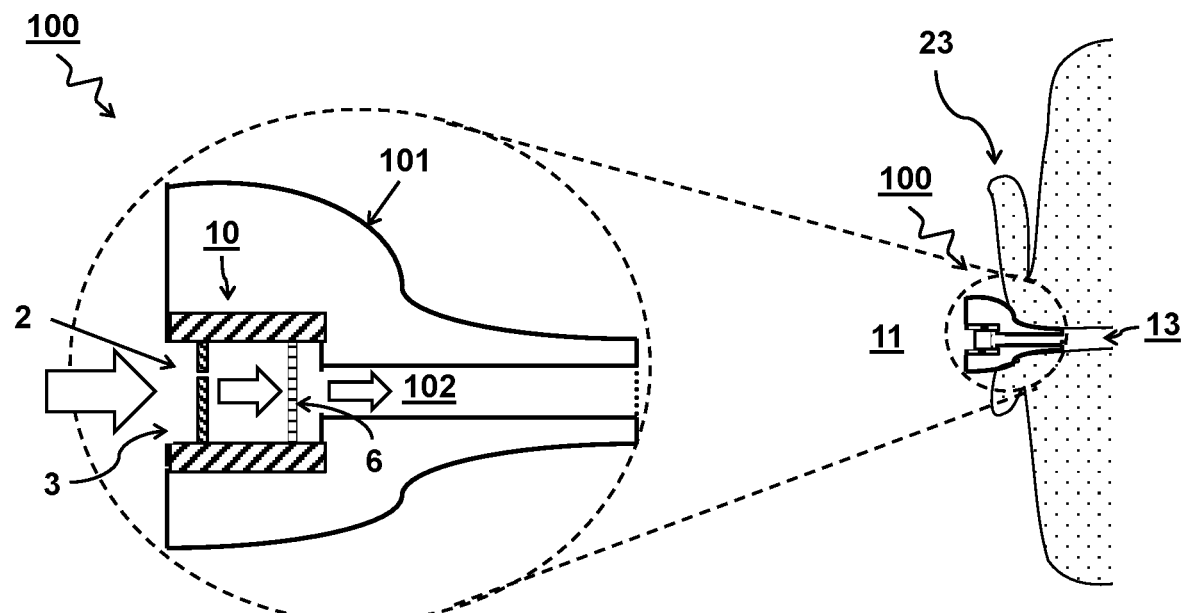
FIG. 7A shows a schematic cross section view of an embodiment of an earplug and how this can be inserted into an ear canal.
Figure 7B:
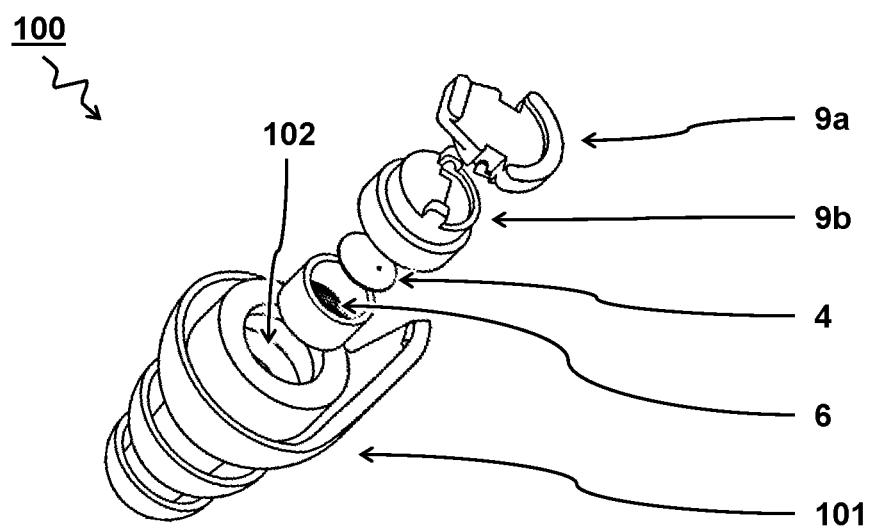
FIG. 7B shows an exploded view of an embodiment of an earplug.

FIG. 7 shows two embodiments for an earplug 100 for hearing protection comprising an acoustic valve 10, as described herein. The ear plug 100 comprises a tip 101 with an outer contour for sealingly fitting into an auditory canal 13 of a user. FIG. 7A shows a cross section view of an embodiment for an earplug 100 with a user customized tip 101 (e.g. otoplastics) while FIG. 7B shows an exploded view of an embodiment with a more universal tip 101, e.g. comprising ridges. The tip 101 comprises a channel 102 through the tip 101. The acoustic valve 10 can be arranged in the channel 102. The channel 102 with the valve 10 arranged therein may in use form an acoustic passage between the external surroundings 11 and the auditory canal 13. For example, in FIG. 7A, right side, the earplug 100 is shown inserted into an ear 23 of a user. As shown in FIG. 7B, the earplug 100 and/or valve 10 may comprise an optional cap (formed in this case by hinging parts 9a, 9b) to manually close off the ear plug passage It is noted that hearing protection can be defined for example in accordance with a minimum attenuation provided by an ear plug or acoustic valve. In one embodiment, when tested in accordance with EN 13819-2:2002, 4.2, the values (Mf−sf) of the ear-plugs are not less than the values given in Table 1 of this standard (reproduced below), wherein Mf are the mean attenuation data and sf the standard deviations as measured in accordance with EN 13819-2: 2002, 4.2. Alternatively, or in addition, also other definitions of hearing protection can be used.

| | Frequency in Hz | | | | | | |
|---|---|---|---|---|---|---|---|
| | 125 | 250 | 500 | 1000 | 2000 | 4000 | 8000 |
| (Mf-sf) in dB | 5 | 8 | 10 | 12 | 12 | 12 | 12 |

The sound pressure level (SPL) typically refers to a logarithmic measure of the effective sound pressure of a sound relative to a reference value. It may be measured e.g. in decibels (dB) above a standard reference level, e.g. 20 μPa root mean square in air or 1 μPa under water. These and other reference levels may be defined e.g. in a standard such as ANSI S1.1-1994. For example, a measurement can be done directly in front of and/or directly behind the ear plug. Measurements can be compared to determine a attenuation level of the ear plug, e.g. expressed as the relative sound pressure levels in decibels. It is noted that the amount of attenuation can be vary as a function of the sound pressure level and/or as function of sound frequency. In some measurements, the sound pressure level and/or the amount of attenuation can be integrated, e.g. over a range of frequencies. The individual or total sound pressure level can also be weighted depending on a typical sensitivity curve of human hearing.

Figure 8A:
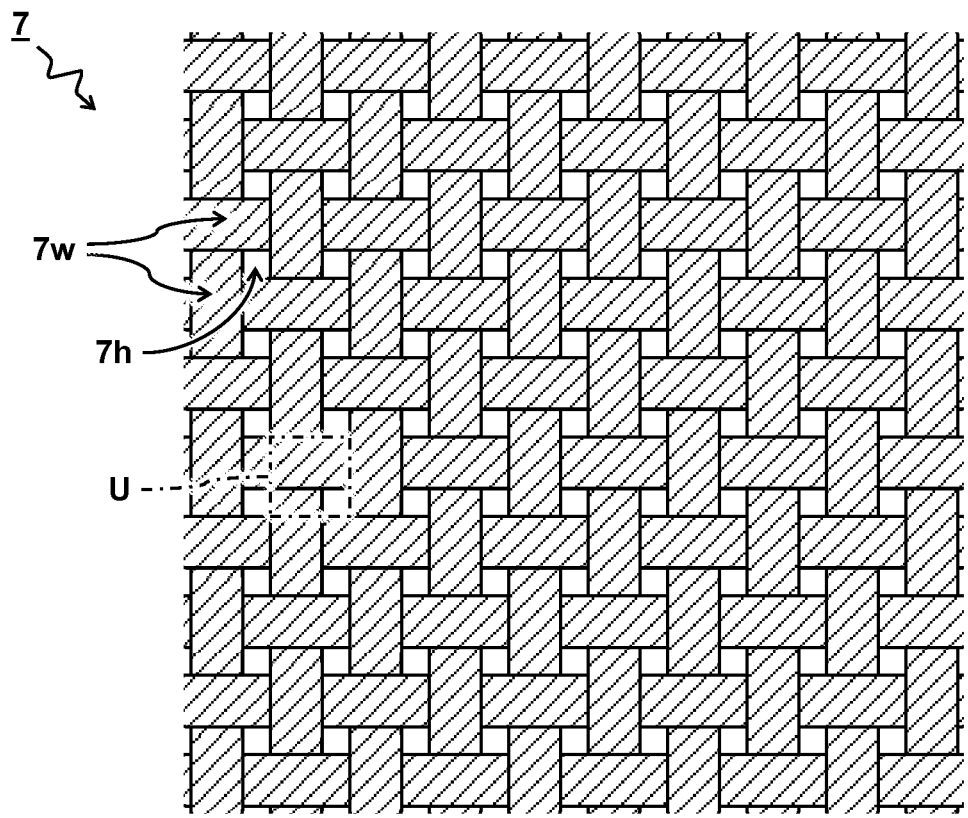
FIG. 8A schematically shows a plan view of a woven mesh.

FIG. 8A schematically shows a plan view of a woven mesh 6 comprising mesh wires 6w forming mesh openings or holes 6h there between. The dash-dotted square "U" in the figure indicates one unit cell that may be considered as a repeating pattern within the mesh 6.

Figure 8B:
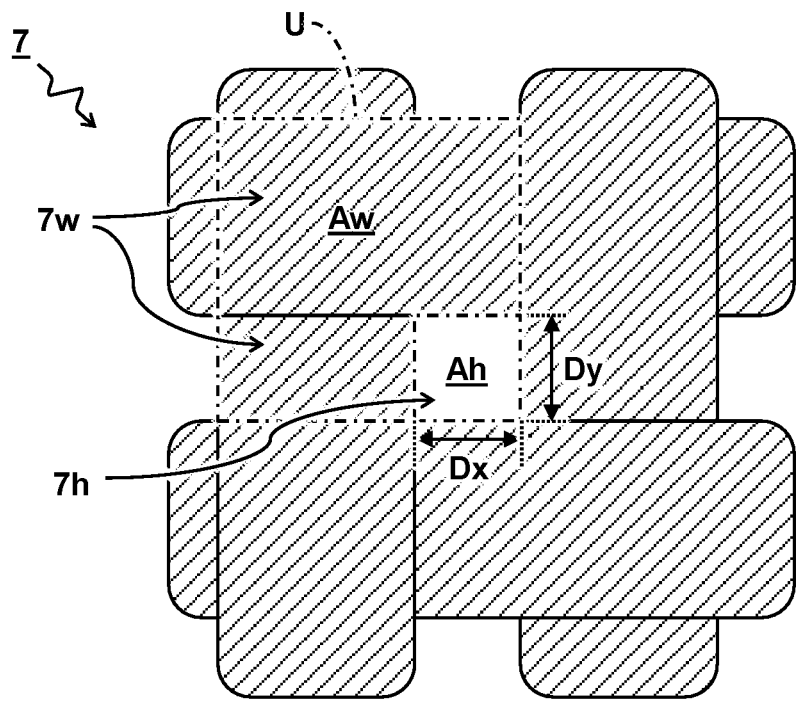
FIG. 8B schematically shows a close-up view of mesh wires.

FIG. 8B schematically shows a close-up view of four mesh wires 6w defining a mesh opening 6h there between. The cross-sections surface area of the wires 6w within the unit cell "U" is indicated as the area "Aw". The cross-sections surface area of the opening 6h within the unit cell "U" is indicated as the area "Ah". As described herein it is found advantageous that the mesh 7 comprises a grid forming a plurality of openings through the grid, wherein a cross-section surface of the openings is between 0.5 to 20 percent of the total cross-section surface of the mesh 7. This may be the case for example for a mesh as depicted wherein $0.005 \leq Ah/(Ah+Aw) \leq 0.2$.

Figure 9A:
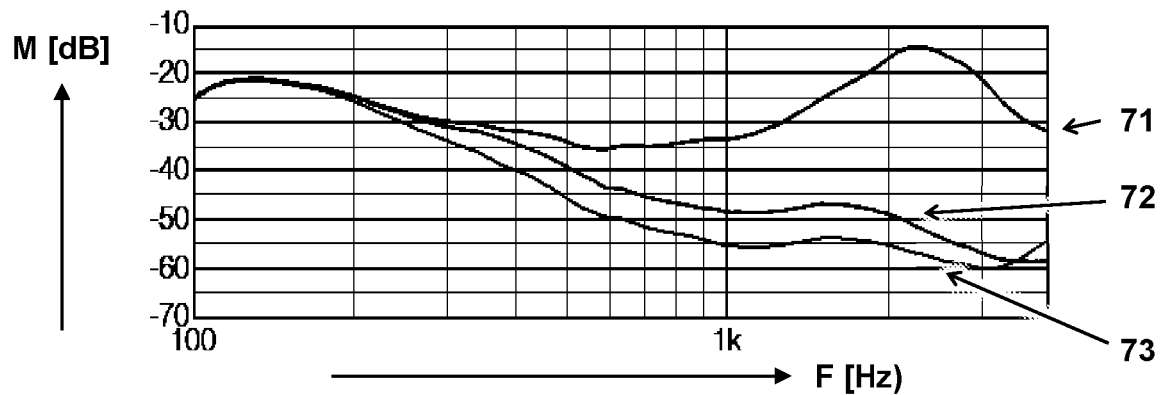
FIGS. 9A and 9B show a graphs of acoustic transfer functions.

FIG. 9A shows a graph of acoustic transfer functions of the sound magnitude M (in decibel) for three different measurements in a frequency range F between 100 and 4000 Hz (corresponding to speech). Reference numeral 71 indicates the response for an open artificial ear, i.e. without ear plug. Reference numeral 72 indicates the response for an impulse protector based on a mesh and perforated disc as described herein. Reference numeral 73 indicates the response for an impulse protector based on two perforated discs. It will be appreciated that the graph 72 of the impulse protector based on a mesh and perforated disc has an acoustic transfer functions that is considerably more flat than the graph of the impulse protector based on two perforated discs 73. The graph 72 thus more closely resembles the graph 71 of the open artificial ear and therefore corresponds to a more natural hearing experience e.g. with less occlusion effect.

Figure 9B:
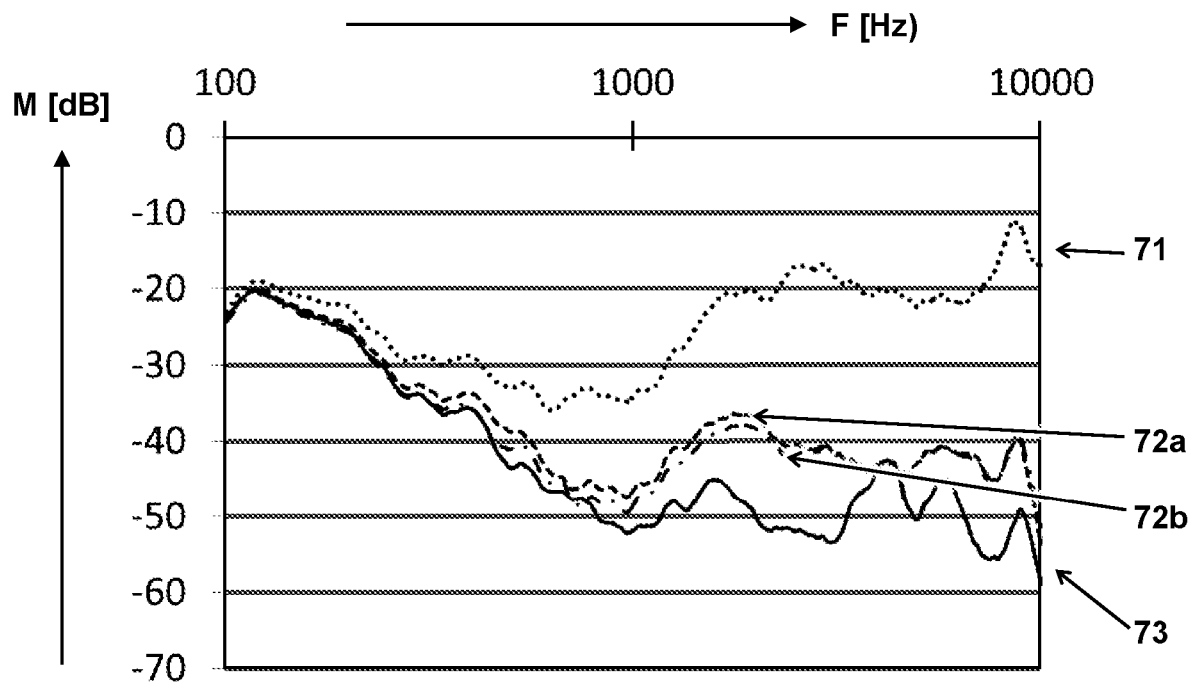

FIG. 9B show further graphs of acoustic transfer functions for different measurements of impulse filters. Reference numerals 71 indicates the response for an open artificial ear. Reference numerals 73 indicates the response for a 200 μm diameter hole. Reference numerals 72a and 72b indicate the respective responses for a first mesh with 20 μm holes (total diameter of the mesh 1.6 mm) and a second mesh with 6 μm holes (total diameter 4 mm). These graphs again illustrate that the mesh provides an improved (flatter) acoustic transfer function, more similar to the open ear than the plate with a single hole.

Without being bound by theory, to improve understanding of different impulse filters and as guidance for optimal parametrization, the following observations are made with regards to the acoustic properties of a densely woven mesh.

In general, sound attenuation in order to protect the ear can be realised by blocking (part of) the ear canal. This could e.g. be done by only allowing sound to enter though a small hole, a pipe or a bunch of small holes. In all those options, the acoustic properties of the openings can be described by two parameters: the acoustic mass ma and the acoustic resistance Ra. (Both have their equivalent in electricity as inductance and resistance.) The acoustic resistance Ra of a circular opening with a radius of "a" can be calculated as follows with "η" the viscosity of air and "L", the depth of the opening in the sound direction:

$$R_a = 8\eta L / (\pi a^4) \quad (1)$$

The acoustic mass of a circular opening can be calculated as follows with "ρ" the density of air:

$$M_a = 4\rho L / (3\pi a^2) \quad (2)$$

Formulas (1) and (2) combined give for the ratio of ma and Ra:

$$M_a / R_a = (\rho / 6\eta) \cdot a^2 \quad (3)$$

This ratio can be important for the acoustic performance of the sound attenuator. For most application it is considered to be beneficial to have acoustic transfer function that has an equal attenuation over the frequency range of speech. (100 Hz-4000 Hz). However, when using openings as described above, the attenuation is higher for higher frequencies. If the acoustic mass term $M_a$ is relatively high, compared to the resistive term $R_a$, the higher frequencies are even more attenuated. Hence it is found desirable to make the ratio as low as possible. If we look at formula (3), this means that the radius a of the holes should be as small as possible. In other words, for a required attenuation of e.g. 10 dB at 500 Hz, it would be preferred to have more smaller holes over less bigger holes.

Precision woven meshes made for filtration and use in acoustic applications are in general made of a specific pattern made from two or more layers of plastic wires woven together. This will result in very many, very small holes. From the discussion above it is clear that for use in a hearing protector, it would be preferred to have a mesh like this over a single hole, since the single hole will lead to a less attractive response.

In the table below, the ratio is calculated for two different mesh types and a hole with a similar resistance $R_a$ as mesh Type A. It is clear that the ratio of $M_a/R_a$ is higher for the hole.

|  | $R_a$ | $M_a$ | $M_a/R_a$ |
| --- | --- | --- | --- |
| Type a (13% mesh openings) | 1.0 * 10^7 | 50 | 5.0 * 10^-6 |
| Type b (5% mesh openings) | 6.0 * 10^7 | 125 | 2.1 * 10^-6 |
| Hole (a = 0.24 mm, L = 1 mm) | 1.0 * 10^7 | 8846 | 8.9 * 10^-4 |

In view of these and other considerations, the inventors find that an optimal combination of sufficient hearing protection and a relatively flat acoustic transfer function can be obtained by providing an acoustic valve 10 with impulse filter as described herein having a combination of a perforated rigid plate 4 and a mesh 7, wherein the openings 7h of the mesh have a cross-section diameter Dx between 0.1 and 70 micrometre, preferably between 1 and 40 micrometre, more preferably between 5 and 30 micrometre. For example, as indicated in FIG. 8B, for a square or rectangular hole 7h, the cross-section diameter may correspond to a length and/or width dimension of the hole, indicated by "Dx" and "Dy".

For example, for round openings (not shown) it is preferably to have a radius "a" (half the diameter) between 0.05 an 35 micrometre.

For the purpose of clarity and a concise description, features are described herein as part of the same or separate embodiments, however, it will be appreciated that the scope of the invention may include embodiments having combinations of all or some of the features described. In one aspect, the present disclosure provides a passive acoustic filter with in series a single disc. The single disc consist of a thin element positioned in series with an other acoustic element providing a desired acoustic characteristic at sound levels below 130 dBA, in particular in combination with universal tip or custom mould. The disc provides a strong increase in attenuation for higher sound levels as a result of a small hole. This hole can be tuned to provide more or less non-linear behaviour having limited effect on the attenuation at lower sound-levels. For example, while embodiments were shown for acoustic valves comprising passive elements, also alternative ways may be envisaged by those skilled in the art having the benefit of the present disclosure for achieving a similar function and result. For example, alternative sequences of the rigid plate, flexible membrane and/or mesh may provide alternative or additional advantages.

Acoustic elements may be combined or split up into one or more alternative components. For example, variable passive filters and/or active elements such as one or more controllable valves may be combined with the rigid disc in addition to, or instead of, the mesh and/or flexible membrane. The various elements of the embodiments as discussed and shown offer certain advantages, such as providing a simple design hearing protection providing a more natural sensation of the environment. Of course, it is to be appreciated that any one of the above embodiments or processes may be combined with one or more other embodiments or processes to provide even further improvements in finding and matching designs and advantages. It is appreciated that this disclosure offers particular advantages to hearing protection and in general can be applied for any application wherein it is desired to improve an acoustic transfer function of a hearing device.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. An acoustic valve for hearing protection, the valve comprising a housing placeable or integrated in an ear plug configured to form a seal between an external surrounding on an entry side of the valve, and an auditory canal of an ear on an exit side of the valve upon placement of the ear plug with the valve into the ear, the housing comprising a sound passage, an impulse filter provided within the sound passage, and an acoustic filter provided within the sound passage;

wherein the sound passage extends through the housing for allowing at least partial transmission of sound from the external surrounding into the auditory canal when the ear plug with the valve is placed into the ear;

wherein the impulse filter comprises:

a rigid plate having an outer plate surface facing the entry side of the valve and an inner plate surface, opposite the outer plate surface and facing the exit side of the valve, the rigid plate having at least one perforation for passing the sound from the external surrounding via the at least one perforation through the rigid plate, wherein a thickness of the rigid plate at a location surrounding the at least one perforation is between 0.05 and 0.5 millimetres and a total perforated cross-section area of the at least one perforation in the rigid plate is between 0.01 and 0.10 square millimetres, and an enclosed volume formed between the rigid plate and the acoustic filter, wherein the enclosed volume is between 5 to 20 cubic millimetres, wherein the at least one perforation forms an open air connection between the external surrounding and the enclosed volume, wherein a cross-section area of the enclosed volume adjacent the rigid plate is larger than a total perforated cross-section area of the at least one perforation through the rigid plate such that the enclosed volume is bounded on the entry side of the valve by the inner plate surface of the rigid plate surrounding the at least one perforation;

wherein the acoustic filter comprises a mesh for flattening an acoustic transfer function of sound into the auditory canal when the ear plug with the valve is placed into the ear, the acoustic filter being between the rigid plate and the exit side of the valve, wherein the mesh comprises a grid forming a plurality of openings through the grid, wherein a cross-section area of the openings is between 0.5 to 20 percent of a total cross-section surface of the mesh such that the enclosed volume is bounded on the exit side of the valve by the grid of the mesh.

2. The acoustic valve according to claim 1, wherein the openings of the mesh have a cross-section diameter between 0.1 and 70 micrometres.

3. The acoustic valve according to claim 1, wherein the mesh is a woven mesh.

4. The acoustic valve according to claim 1, wherein the rigid plate is an integral part of the housing.

5. An ear plug for hearing protection comprising a tip with an outer contour for sealingly fitting into an auditory canal of a user, wherein the tip comprises a channel through the tip, and wherein an acoustic valve is arranged in the channel, the valve comprising a housing placeable or integrated in the ear plug configured to form a seal between an external surrounding on an entry side of the valve, and an auditory canal of an ear on an exit side of the valve upon placement of the ear plug with the valve into the ear, the housing comprising a sound passage, an impulse filter provided within the sound passage, and an acoustic filter provided within the sound passage;

wherein the sound passage extends through the housing for allowing at least partial transmission of sound from the external surrounding into the auditory canal when the ear plug with the valve is placed into the ear;

wherein the impulse filter comprises:

a rigid plate having an outer plate surface facing the entry side of the valve and an inner plate surface, opposite the outer plate surface and facing the exit side of the valve, the rigid plate having at least one perforation for passing the sound from the external surrounding via the at least one perforation through the rigid plate, wherein a thickness of the rigid plate at a location surrounding the at least one perforation is between 0.05 and 0.5 millimetres and a total perforated cross-section area of the at least one perforation in the rigid plate is between 0.01 and 0.10 square millimetres, and an enclosed volume formed between the rigid plate and the acoustic filter, wherein the enclosed volume is between 5 to 20 cubic millimetres, wherein the at least one perforation forms an open air connection between the external surrounding and the enclosed volume, wherein a cross-section area of the enclosed volume adjacent the rigid plate is larger than a total perforated cross-section area of the at least one perforation through the rigid plate such that the enclosed volume is bounded on the entry side of the valve by the inner plate surface of the rigid plate surrounding the at least one perforation;

wherein the acoustic filter comprises a mesh for flattening an acoustic transfer function of sound into the auditory canal when the ear plug with the valve is placed into the ear, the acoustic filter being between the rigid plate and the exit side of the valve, wherein the mesh comprises a grid forming a plurality of openings through the grid, wherein a cross-section area of the openings is between 0.5 to 20 percent of a total cross-section surface of the mesh such that the enclosed volume is bounded on the exit side of the valve by the grid of the mesh.

6. The acoustic valve according to claim 1, wherein the enclosed volume is less than 15 cubic millimetres.

7. The acoustic valve according to claim 1, wherein a thickness of the rigid plate at a location surrounding the at least one perforation is between 0.1 and 0.3 millimetres.

8. The acoustic valve according to claim 1, wherein the rigid plate has a single perforation for passing the sound from the external surrounding.

9. The acoustic valve according to claim 8, wherein the single perforation is positioned off-center with respect to the housing.

10. The ear plug according to claim 5, wherein the enclosed volume is less than 15 cubic millimetres.

11. The ear plug according to claim 5, wherein the rigid plate has a single perforation positioned off-center with respect to the housing.

12. The acoustic valve according to claim 1, wherein the impulse filter provided within the sound passage is configured to attenuate impulse sound above 130 dB from the external surrounding into the auditory canal.

13. The acoustic valve according to claim 1, wherein the impulse filter is configured to pass sound from the external surrounding via the at least one perforation through the rigid plate, into the enclosed volume, and then through the mesh before entering into the auditory canal to provide the impulse filter with a specific sequence of filtering.

14. The acoustic valve according to claim 13, wherein the impulse filter is configured, by the thickness of the rigid plate, by a volume of the enclosed volume, and by the specific sequence of filtering, to attenuate impulse sound with an input sound pressure level between 140 and 160 dB at an entrance of the sound passage to an output sound pressure level below 140 dB at an other end of the sound passage and into the auditory canal.

15. The acoustic valve according to claim 13, wherein the impulse filter is configured such that the sound can pass substantially unobstructed from the external surrounding through the at least one perforation of the rigid plate into the enclosed volume.

16. The acoustic valve according to claim 13, wherein the housing has inner walls defining the cross-section area of the enclosed volume, and wherein the enclosed volume is defined between the inner plate surface of the rigid plate, grid of the mesh, and the inner walls of the housing.

17. The ear plug according to claim 5, wherein the impulse filter is configured to pass sound from the external surrounding via the at least one perforation through the rigid plate, into the enclosed volume, and then through the mesh before entering into the auditory canal to provide the impulse filter with a specific sequence of filtering.

18. The ear plug according to claim 17, wherein the impulse filter is configured such that the sound can pass substantially unobstructed from the external surrounding through the at least one perforation of the rigid plate into the enclosed volume.

19. The ear plug according to claim 17, wherein the housing has inner walls defining the cross-section area of the enclosed volume, and wherein the enclosed volume is defined between the inner plate surface of the rigid plate, the grid of the mesh, and the inner walls of the housing.

20. The acoustic valve according to claim 1, wherein the acoustic filter comprises a flexible membrane, wherein a distance between the flexible membrane and the mesh at equilibrium is less than 0.15 millimetre, wherein the flexible membrane is arranged for abutting the mesh at sound pressure levels in the enclosed volume above 120 dB.

* * * * *